United States Patent
Kumar et al.

[11] Patent Number: 5,925,043
[45] Date of Patent: Jul. 20, 1999

[54] ELECTROSURGICAL ELECTRODE WITH A CONDUCTIVE, NON-STICK COATING

[75] Inventors: B. Ajit Kumar; Don B. Olsen, both of Salt Lake City, Utah

[73] Assignee: MedQuest Products, Inc., Salt Lake City, Utah

[21] Appl. No.: 08/846,268

[22] Filed: Apr. 30, 1997

[51] Int. Cl.⁶ .................................................. A61B 17/39
[52] U.S. Cl. .............................. 606/45; 606/48; 606/49; 606/50; 29/825
[58] Field of Search .............................. 606/41, 45, 48, 606/49, 50, 51, 52; 29/825

[56] References Cited

U.S. PATENT DOCUMENTS

| 5,380,320 | 1/1995 | Morris | 606/45 |
| 5,549,604 | 8/1996 | Sutcu et al. | 606/45 |
| 5,658,282 | 8/1997 | Daw et al. | 606/49 |
| 5,697,926 | 12/1997 | Weaver | 606/45 |
| 5,720,775 | 2/1998 | Larnard | 606/41 |

FOREIGN PATENT DOCUMENTS

479482   4/1992   European Pat. Off. .................. 606/45

*Primary Examiner*—Lee Cohen
*Attorney, Agent, or Firm*—Thorpe, North & Western, L.L.P.

[57] ABSTRACT

An electrosurgical blade is provided having a ceramic coating which is conductive, flexible and provides a surface which inhibits the build up of charred tissue. These properties enable the electrosurgical blade to deliver controlled amounts of radio-frequency energy to tissue. The manufacturing process produces a coating of titanium nitride on a stainless steel blade which is amorphous, enabling the electrosurgical blade to bend with the blade in order to perform a wide variety of surgical procedures without damaging the coating. The electrosurgical blade can therefore be used to efficiently cut, coagulate, fulgurate and desiccate tissue. While the blade is primarily used in the monopolar mode, the present invention also encompasses at least two electrosurgical electrodes having the same ceramic coating as the electrosurgical blade, and used in the bipolar mode for coagulation. The coating can be applied on a variety of shapes of electrocautery instruments.

29 Claims, 3 Drawing Sheets

ELECTROSURGICAL ELECTRODE WITH A CONDUCTIVE, NON-STICK COATING

BACKGROUND OF THE INVENTION

1. Field of the Invention

This invention pertains to a electrosurgical instrument and a method for its manufacture. More specifically, the present invention pertains to a disposable and/or reusable electrosurgical blade which inhibits the build up of charred tissue, and is therefore able to slide through tissue when making an incision, and perform cauterization functions with a minimal amount of thermal damage to surrounding tissues.

2. State of the art

State of the art electrosurgical blades are utilized in surgery to provide both a blade for incising through normal tissue and for excising abnormal tissue. The electrosurgical blade directs a source of radio-frequency (RF) energy to the tissue to thereby perform cauterizing (hemostasis) functions such as coagulation, fulguration and desiccation. Ideally, the electrosurgical blade is utilized to effectively cut tissue while at the same time minimizing the amount of bleeding.

The amount and type of radio frequency energy delivered to tissue through the electrosurgical blade is varied depending upon the activity being performed. Cutting is achieved primarily with a continuous sinusoidal waveform. In contrast, coagulation is performed with a series of sinusoidal wave packets. The clinician is ideally able to elect one of these waveforms, or a blend of them for a particular surgical procedure.

An electrosurgical blade can operate in one of two modes which are defined by the method by which electrical current enters and leaves the tissue. In a monopolar mode, the current flows from a small active electrode (the electrosurgical blade), spreads through the body, and returns to a large dispersive electrode on the skin. In contrast, the bipolar mode delivers electrical current to tissue which is disposed between two electrodes which are generally spaced apart to form a gap. The monopolar mode is used for both cutting and coagulation, and the bipolar mode is used primarily for coagulation.

While using electrosurgical instruments, tissue is inevitably charred during surgery and will try to cling to the heat source. When the heat source is the electrosurgical blade, the charred tissue interferes with the performance of the electrosurgical blade. Performance degradation of the blade poses serious problems when trying to minimize heat damage to a patient's tissues.

One of the specific problems which electrosurgical blades presently suffer from and which is caused by the build up of charred tissue is that cutting efficiency is reduced. The typical response to such residual tissue build up is to increase current to the electrosurgical blade to compensate. However, increased current poses a more serious shock hazard to the patient as well as the physician. It also raises the possibility of more easily and rapidly charring tissue. This is because some exposed surfaces of the electrosurgical blade will have charred tissue adhering thereto, but other surfaces will be free of charred tissue and will therefore deliver more current to tissue at a faster rate.

Another problem resulting from the build up of charred tissue is that the charred tissue can fracture off of the blade. The fractured tissue becomes an undesired foreign body within the surgical field. The fractured tissue can then interfere with the surgical procedure being performed, increase the inflammatory response, and delay the healing process.

The build up of charred tissue also causes the electrosurgical blade to pass through tissue with increasing resistance or drag. This drag tends to distort the tissue and consequently alter anatomical relationships. This can create problems when suturing after the surgical procedure, and possibly delay healing, and result in more visible scarring.

The burning of charred tissue also generates hazardous smoke plumes. Inhalation of the smoke endangers those performing a surgical procedure.

The consequence of the build up of charred tissue is that the procedure is interrupted, while the electrosurgical blade must either be replaced, or passed to an operating room (OR) technician who scrapes off the build up before the clinician continues with the surgical procedure.

The problems described above have been dealt with by various electrosurgical blades. For example, prior U.S. patents have been issued for various electrosurgical blades which apply a non-stick coating to a cutting edge of the blade. These blades typically suffered from small openings in the non-stick coating which were intentionally allowed to form in order to ensure electrical conductivity along the cutting edge. Exposing the metallic surface of the blade resulted in charred tissue sticking to these areas. The result was that the blade quickly becomes non-conductive and consequently unusable.

Figure 1:
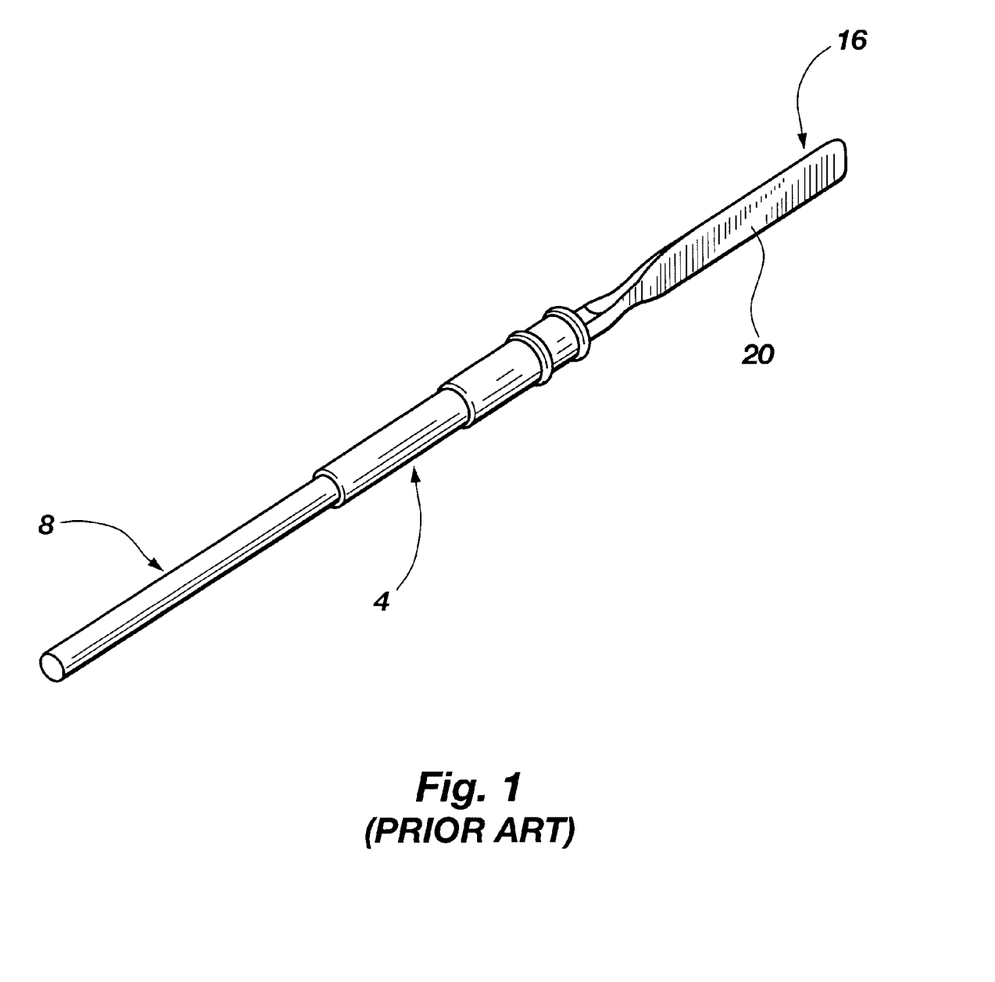
FIG. 1 is a perspective view of an electrosurgical blade typical of the prior art.

In an attempt to improve the blade, Blanch was granted U.S. Pat. No. 4,785,807 (the '807 patent) for teaching an electrosurgical blade which has a cutting edge of the blade which is abraded or etched, and a coat of a non-stick fluorinated hydrocarbon material which is applied over the etched cutting edge. This electrosurgical blade is shown in FIG. 1. The blade 4 is shown with a proximal end 8 and a distal end 16. A coating 20 of non-stick material covers the surface area of the cutting blade and is intended to eliminate or reduce the clinging of charred tissue to the blade. By eliminating the small openings in the non-stick coating of previous blades, the blade 4 better inhibited the build up of charred tissue. However, one drawback in the principle of the '807 patent is that the non-stick coating 20 is not particularly durable, and will wear off after repeated usage. This is true partly because the non-stick and non-conductive coating 20 has the properties of an insulator and had to be kept thin in order to enable the radio-frequency energy to pass through the non-stick coating 20 to the tissue to cut and/or cauterize.

Another drawback of the blade described in the '807 patent is that the non-stick coating is not flexible. This inability to bend the electrosurgical blade seriously limits the options of the surgeon in the surgical procedures in which the blade can be used. Furthermore, bending the electrosurgical blade causes the non-stick coating to fracture. The electrosurgical blade then begins to rapidly build up charred tissue because of exposed etched metal of the blade, and any advantages of the non-stick coating are lost.

The non-stick coating of the '807 patent is also specifically described as Teflon™. The nature of Teflon™ is such that it requires a high current to be used in cutting and cauterization. This is because electrical current must pass through the Teflon™ to the tissue. However, this constant passage of current eventually breaks down the Teflon™, leaving small holes or other imperfections in the Teflon™ coating. Charred tissue then begins to adhere to the exposed metal beneath the Teflon™ coating. Furthermore, electrical current will no longer be uniform across the blade because the current will tend to concentrate at locations where the metal is exposed.

The state of the art includes at least one electrosurgical blade which is made of a ceramic. The ceramic is used as an insulator on which a tungsten wire is placed on a cutting edge of the ceramic blade. Radio frequency energy is then applied to the tungsten wire which facilitates cutting of tissue. However, this ceramic blade cannot be bent and does not provide a flat surface for cauterization, so its application to a variety of different surgical procedures is very limited.

It is also a typical perception that ceramics do not make a good electrosurgical blade because ceramics exhibit properties of brittleness, inflexibility, and act as insulators rather than conductors of electrical or radio frequency energy.

Another state of the art electrosurgical blade is fashioned from a polymer. The polymer is doped with conductive particles to make it conductive of the radio frequency energy which is used to heat tissue. A trend toward using plastics was most likely fostered by the view that plastics are inexpensive, the property of lubricity of plastics is desirable in electrosurgical blades, and the process of applying plastic as a coating is relatively simple.

Another problem in the state of the art electrosurgical blades which utilize Teflon™ is that when heated, Teflon disadvantageously breaks down and evolves fluorine as a gas. This gas is hazardous to the patient and the surgical team.

It would be an advantage over the state of the art to provide, among other things, an electrosurgical blade which better inhibits the build up of charred tissue, provides a more durable non-stick coating which can withstand repeated use and cleaning, and which provides an amorphous or amorphous-like conductive coating which enables the electrosurgical blade to bend so as to perform a larger variety of surgical procedures at low power levels, without the risk of damaging or breaking down the coating and causing tissue build up. It would be a further advantage to provide a protective coating which does not evolve gases when heated.

OBJECTS AND SUMMARY OF THE INVENTION

It is an object of the present invention to provide an electrosurgical blade which inhibits the build up of charred tissue.

It is another object to provide an electrosurgical blade which has a non-stick coating which will not burn off, wear away or scrape away after repeated use.

It is another object to provide an electrosurgical blade which has a non-stick coating which can flex with the material on which it is applied to thereby be more versatile in surgical procedures.

It is another object to provide an electrosurgical blade which includes a generally flat surface for performing various cauterization functions.

It is another object to provide an electrosurgical blade which maintains power levels relatively constant because the power console does not have to compensate for the build up of charred tissue.

It is another object to provide an electrosurgical blade which reduces plumes generated from burning tissue while cutting and cauterizing, and from breakdown of the coating.

It is another object to provide an electrosurgical blade which uses a ceramic as a non-stick coating over the entire active surface of the electrosurgical blade, and not limited to a cutting edge.

It is another object to provide an electrosurgical blade which uses a conductive ceramic as the non-stick coating.

It is another object to provide an electrosurgical blade which uses an amorphous ceramic coating which can flex without breaking or detaching itself from a substrate.

It is another object to provide a surface that does not scrape off because of cleaning during the surgical process.

It is another object to provide an electrosurgical blade which provides increased safety regarding electrical hazards to the patient and the clinician by keeping power levels at relatively low and constant levels.

It is another object to provide an electrosurgical blade which is capable of fulguration without destroying the coating on the base metal substrate.

It is another object to provide an electrosurgical blade which minimizes thermal damage to tissues by providing a blade which better inhibits the build up of charred tissue and provides a more uniform and consistent cut at lower radio frequency energy levels.

It is another object to provide an electrosurgical blade which uses transition metal nitrides, carbides and oxides as the ceramic coating.

It is another object to provide an electrosurgical blade which has the ceramic coating applied through sputtering to produce an amorphous ceramic coating.

It is another object to provide an electrosurgical blade which is cost effective to produce, and simple and efficient to manufacture.

In accordance with these and other objects of the present invention, the advantages of the invention will become more fully apparent from the description and claims which follow, or may be learned by the practice of the invention.

The present invention provides in a preferred embodiment an electrosurgical blade with a ceramic coating which is conductive, flexible and provides a surface which inhibits the build up of charred tissue. These properties enable the electrosurgical blade to deliver controlled amounts of radio-frequency energy to tissue. The manufacturing process produces a coating of titanium nitride on a polished stainless steel blade which is amorphous, enabling the electrosurgical blade to bend in order to perform a wide variety of surgical procedures. The electrosurgical blade can therefore be used to efficiently cut, coagulate, fulgurate and desiccate tissue. While the blade is primarily used in the monopolar mode, the present invention also encompasses electrosurgical electrodes having the same ceramic coating as the electrosurgical blade, and used in the bipolar mode for coagulation.

In accordance with one aspect of the present invention, the conductivity of the amorphous ceramic coating enables the electrosurgical blade to perform fulguration which normally destroys coatings of other blades. Accordingly, the present invention is a versatile surgical instrument.

In another aspect, the performance of the electrosurgical blade is more consistent in comparison to other blades because the build up of charred tissue is much slower, and after cleaning, the ceramic coating on the electrosurgical blade returns to the same state of lubricity.

Another aspect of the invention is the considerably improved durability of the ceramic coating. Unlike other coatings, the present invention does not burn away or flake or scrape off after repeated use, thereby making the electrosurgical blade more cost effective as well as more versatile.

In another aspect, thermal tissue damage is minimized because the current required to operate the electrosurgical blade consistently remains at lower levels because the build up of charred tissue is substantially slowed and minimized, and there is no insulating barrier to overcome because the coating is conductive.

In another aspect of the invention, plume reduction is accomplished by preventing the build up of charred tissue which is a major source of smoke. In a related aspect, introduction of foreign body contamination into the surgical field is also reduced when there is no charred tissue to flake off the electrosurgical blade.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of one preferred embodiment of the present invention will be given numerical designations and in which the preferred embodiment of the invention will be discussed so as to enable one skilled in the art to make and use the invention.

Before describing the physical characteristics of the present invention, it is useful to examine more closely the most important functions which it is designed to fulfill. Specifically, the present invention is designed to be an improvement over the prior art in that it is safer to use, it provides effective cutting with minimal thermal damage to incised tissue, fulguration must be accomplished with ease, and there must be a reduction in the smoke generated during surgery (plume reduction). As the present invention is shown, it will be explained how the new electrosurgical instrument accomplishes these functions.

Beginning by setting forth the physical design of the preferred embodiment, the present invention is embodied in the electrosurgical blade to be described below. Later, a method of manufacturing the electrosurgical blade will be presented. The electrosurgical blade is illustrated in a preferred embodiment in FIG. 2A. The preferred embodiment is an electrosurgical blade 100 comprised of a base metal substrate 102 with a ceramic coating 104. It is this ceramic coating 104 and the method of applying it to the base metal substrate 102 which forms the basis of the novelty of the present invention. In the preferred embodiment, the ceramic coating 104 is composed of titanium nitride (TiN) which is applied over the base metal substrate 102 by any appropriate method, such as those to be discussed later.

As stated previously above, ceramic is used in another electrosurgical blade of the prior art, but as an insulator for supporting a wire which functions as a cutting edge. Therefore, despite the perception (which is usually correct) that ceramics exhibit properties of brittleness, inflexibility, and act as insulators rather than conductors of electrical or radio frequency energy, the present invention advantageously uses a different type of ceramic to create the improved electrosurgical blade of the present invention.

Figure 2A:
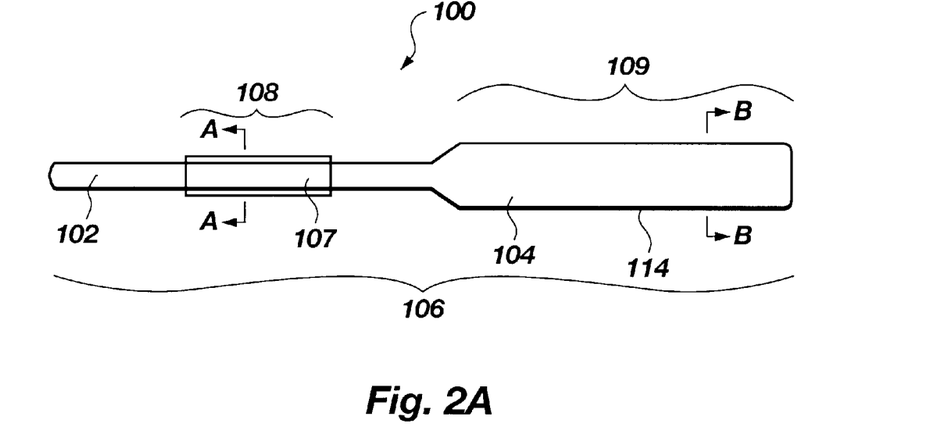
FIG. 2A is a profile view of a preferred embodiment made in accordance with the present invention, wherein an electrosurgical instrument is shown having a cutting edge.

The electrosurgical blade 100 of FIG. 2A has a thin ceramic coating 104 of TiN applied to a cutting and cauterizing portion 109 of the base metal substrate 102 so that the electrosurgical blade 100 can also perform the functions of coagulation, fulguration and desiccation. All these functions can be performed because the ceramic coating 104 does not limit or modify conduction of radio-frequency electrical energy from the electrosurgical blade 100 through the ceramic coating 104 to tissue being cut and/or cauterized. The ceramic coating 104 preferably has a thickness on the order of micrometers as will be explained.

A significant advantage to be addressed later is that the TiN ceramic coating 104 is electrically conductive. What is important structurally is that it becomes necessary to provide an insulated grip 108 to prevent shock to the clinician wielding the electrosurgical blade 100. Any appropriate insulating material 107 (FIG. 2B) can be used for the insulated grip 108 as known to those skilled in the art. For example, rubber or rubberized material will function adequately to cover the exposed metal part 102 of the grip 108. A handle (not shown) is then inserted over the base metal substrate 102 to energize the electrode/blade 100.

The base metal substrate 102 of the electrosurgical blade 100 of the preferred embodiment is preferably a stainless steel blade 106. This is advantageous because the stainless steel blade 106 is already a standard surgical instrument widely available today that fits a standard handle, thus making it inexpensive to obtain. Furthermore, the stainless steel blade 106 is an excellent conductor of the radio frequency energy to be applied to the electrosurgical blade 100.

Figure 2B:
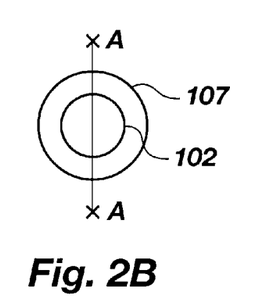
FIG. 2B is a cut-away view of the preferred embodiment from the perspective of line A—A as shown in FIG. 2A.

FIG. 2B is provided to show a cross section of the insulated grip 108 portion of the present invention which is not in proportion with the drawing in FIG. 2A. The base metal substrate 102 is shown in this preferred embodiment as having a circular cross section, and the insulating material 107 is shown to be generally uniform in its thickness around the base metal substrate 102.

Figure 2C:
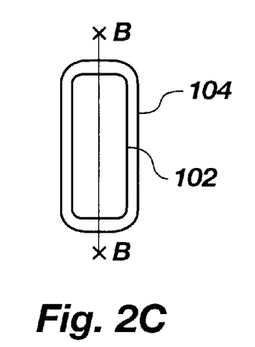
FIG. 2C is a cut-away view of the preferred embodiment from the perspective of line B—B as shown in FIG. 2A.

FIG. 2C is provided to show a cross section of the cutting and cauterizing portion 109 of the present invention which is also not in proportion with the drawing in FIG. 2A. The base metal substrate 102 is shown in this preferred embodiment as having a rectangular cross section, and the ceramic coating 104 is shown to be generally uniform in its thickness around the base metal substrate 102.

Most important to the present invention are the properties of the ceramic coating 104 composed of TiN. It should also be mentioned that while the preferred embodiment uses TiN as the ceramic coating 104, there are other ceramics from the family of ceramics known as transition metal nitrides which might be used in the present invention. These ceramic coating materials include titanium nitride, among others. These materials are classified in terms of properties of hardness, corrosion resistance, color and high spectral reflectance (smoothness). What is important to the preferred embodiment of the present invention is that the material selected for the ceramic coating 104 have the desirable characteristics of TiN. The most important of these characteristics are that the coating (a) be conductive, (b) act amorphous after application to the electrosurgical instrument, and (c) have a high degree of lubricity to thereby flow smoothly through tissue being cut/cauterized. It should also be realized that TiN can be used alone or in combination with other materials having desirable characteristics. These other materials might also include other conductive (transition metal nitrides) or non-conductive ceramics.

Although never applied to a surgical blade before, Titanium Nitride is a ceramic well known for its advantageous properties of hardness, wear resistance, inertness, lubricity and thermal stability in such applications where a low friction interface is needed to protect moving parts from wear. However, it is the properties of electrical as well as thermal conductivity jointly with lubricity which make it attractive as a suitable coating for an electrosurgical blade 100 in the present invention.

The preferred process of manufacturing the electrosurgical blade 100 by applying the TiN to the base metal substrate 102 is the process of sputtering. However, it is helpful to know at this stage that advantageously, the TiN can be applied using sputtering at room or near-room temperatures, significantly simplifying the manufacturing process. TiN can also be applied with high dimensional accuracy to obtain an even coating thickness along all surfaces. Furthermore, TiN exhibits a very high load carrying capacity and toughness. TiN also has excellent adhesion qualities so that it does not spall, even under plastic deformation of the surface. The high toughness and excellent adhesion properties are due to a metallurgical bonding between the stainless steel substrate and the TiN coating Most importantly, however, TiN advantageously has high hardness and low friction coefficients (referred to as lubricity). This property of lubricity enables the electrosurgical blade 100 to glide through tissue for extended periods of time between cleaning. But unlike Teflon™ coatings, TiN will not burn off or wear away quickly from repeated use to leave the base metal substrate 102 exposed. Therefore, the problem of irregular current densities across the surface of the electrosurgical blade 100 is avoided.

When looking at the goals of the present invention as explained at the beginning of the detailed description, it is now appropriate to address a primary aspect of how the TiN ceramic coating 104 makes a safer electrosurgical blade 100. When dealing with an electrosurgical blade, a clinician controls the current supplied thereto. This is because of the different cutting and coagulation functions which the electrosurgical blade 100 performs. As a practical matter, the clinician typically increases the current supplied to the electrosurgical blade 100 to compensate for charred tissue which begins to build up and interfere with the transfer of radio frequency energy to the tissue. However, increasing the current also increases the possibility that too much current will come into contact with the tissue of the patient and cause thermal damage. Therefore, if the electrosurgical blade 100 does not allow charred tissue to accumulate easily, the clinician is not tempted to increase the current when using a clean electrosurgical blade 100. This minimizes the amount of plume produced.

A related aspect is a realization that the blade of the present invention requires less power to begin an operation. This is because prior art blades need to use a higher power setting so that the RF energy being propagated by the blade can pass through the insulating coating. In contrast, the present invention incorporates a conductive coating which enables RF energy to more readily and uniformly reach the tissue.

Furthermore, prior art blades can more easily have gaps in a non-stick coating which expose a base metal substrate. If the clinician is increasing the current and causing high current densities to appear at exposed areas of the base metal substrate, the clinician is in even greater danger of causing thermal damage to tissue. However, because the TiN ceramic coating 104 has a better bond with the base metal substrate 102 in the present invention, there will generally not be any gaps in the TiN ceramic coating 104 where high current densities could accumulate. The result is that there is less likelihood of causing thermal damage to tissue with the present invention.

In a related safety aspect, using electrical current in an operating theater inherently creates risks not only for the patient, but for the clinician and the staff. Therefore, there are substantial advantages in minimizing the amount of electrical current which is required in any surgical procedure, such as reducing the risk of electrical shock and smoke generation and their consequences for all those involved.

To quantify the safety advantages of the present invention as explained above, it is appropriate to examine more specifically how the preferred embodiment of the electrosurgical blade 100 compares to other blades. While other electrosurgical blades may have improved performance in that they initially provide a slick blade, problems still persist which the present invention substantially overcomes. These problems are explained best by showing how the present invention provides a) improved toughness for a longer useful life, b) flexibility, and c) act as a uniform conductor of radio frequency energy.

For example, while prior art electrosurgical blades initially provide a slick surface, the materials used to create the coating wear down to the base metal substrate faster from repeated use, especially from performing fulguration. Furthermore, the wear is typically uneven. However, the ceramic TiN either has no wear, or wears substantially less than, for example, the Teflon™ coating used in the prior art because Teflon™ burns away, peels off the substrate, and has holes punctured through it to the substrate when performing fulguration. Consequently, the present invention has a longer useful lifespan.

Figure 3:
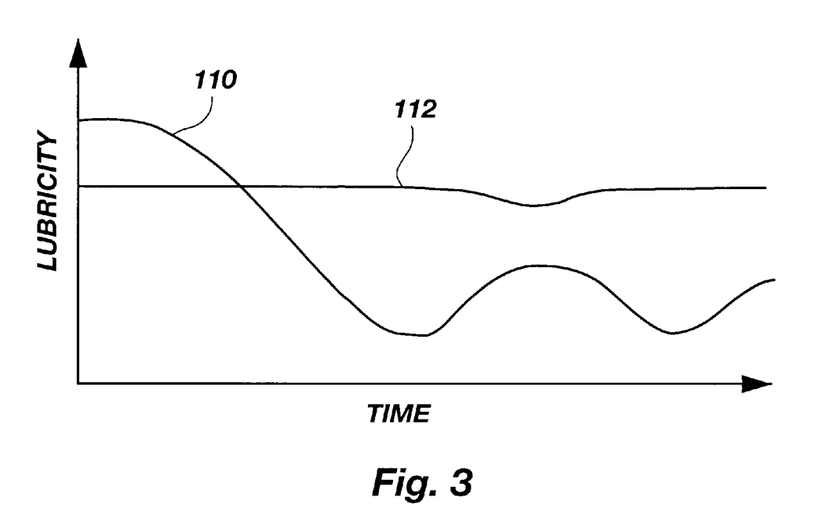
FIG. 3 is a graph comparing lubricity of the present invention to a state of the art electrosurgical blade also using a non-stick coating.

While it is true that all electrosurgical blades will eventually begin to accumulate charred tissue, delaying the build up of tissue leaves the clinician with greater continuity during the surgical procedure. To illustrate this concept of greater continuity in performance, the graph shown in FIG. 3 is provided to show a practical application of the present invention compared to a Teflon™ coated electrosurgical blade. The y-axis is defined as increasing lubricity, and the x-axis is defined as increasing time. Teflon™ performance line 110 represents the performance of a Teflon™ coated electrosurgical blade over time. The Teflon™ performance line 110 shows that Teflon™ begins with a high degree of lubricity, but the line 110 rapidly descends, indicating that the build up of charred tissue is relatively rapid because of the disadvantageous nature and instability of the Teflon™ coating. Just as importantly, it should be noticed that the lubricity of Teflon™ never returns to its initial state of lubricity. In contrast, line 112 shows that the present invention performs more consistently. The line 112 has no great dips in lubricity, and after a quick wiping or scraping of the electrosurgical blade 100, it returns to its initial state of lubricity.

Most advantageously, the TiN ceramic coating 104 of the present invention also has substantially greater flexibility than blades of the prior art. It is the case with the prior art electrosurgical blades that they come with warnings that the electrosurgical blade is not to be bent. Bending will typically result in a coating becoming detached from the base metal substrate because the bond between the base metal substrate and the coating is relatively weak. The detached coating essentially nullifies any advantages the blade initially might have possessed.

In contrast, the present invention has a much stronger bond between the base metal substrate 102 and its ceramic coating 104. This bond extends down to the molecular level. More specifically, there is a metallurgical bonding between the stainless steel blade 106 and the TiN coating. What is created is defined as an interfacial nanometer layer consisting of both the base metal substrate 102 and the TiN ceramic coating 104. This interfacial zone is created in the first stage of the coating process when TiN is sputtered onto the base metal substrate 102. In other words, it is accurate to state that the TiN ceramic coating 104 can be referred to as an amorphous bond, having no crystalline structure subject to fracturing. The amorphous TiN ceramic coating 104 can therefore flex integrally with the base metal substrate 102 to which it is attached. Consequently, the electrosurgical blade 100 of the present invention can substantially outperform prior art blades because of its flexibility. The only limits to the flexibility of the electrosurgical blade 100 are those imposed by the nature of the stainless steel blade 106 underneath the TiN ceramic coating 104.

The importance of flexibility in a surgical blade, let alone in an electrosurgical blade 100, is critical because of the numerous surgical procedures which require that the surgical blade be manipulated in ways which cause it to be bent or deformed. The great advantage of the preferred embodiment of the present invention is thus made apparent when compared with the electrosurgical blades which must not be bent but are in use today.

Other advantages of the electrosurgical blade 100 of the present invention become apparent when examining in detail the specific surgical procedures which can be performed. As mentioned earlier, the functions of cutting, coagulation, fulguration and desiccation are performed with the present invention. This is significant in that electrosurgery is used in about 80 percent of the approximately 18 million surgical procedures which are performed each year.

The function of cutting is the movement of an electrode through tissue while applying electrical current to individual cells. The cells which come in contact with the electrode are vaporized, which sequentially separates the tissue to produce the cutting effect.

The function of coagulation of blood is accomplished by using a less concentrated current to produce heat over a relatively large area. This action causes cellular dehydration and denaturation of proteins instead of vaporization, and thus leads to blood vessel thrombosis.

The function of fulguration is the movement of an electrode above the surface of the skin to produce a spark in the gap. The spark causes carbonization and charring of tissue, which insulates the deep tissue from destruction.

Finally, the function of desiccation is performed using higher voltage but less current to produce cellular dehydration and an electrodesiccating effect. A coagulum of tissue is thus produced by direct contact between an electrode and tissue.

Figure 4:
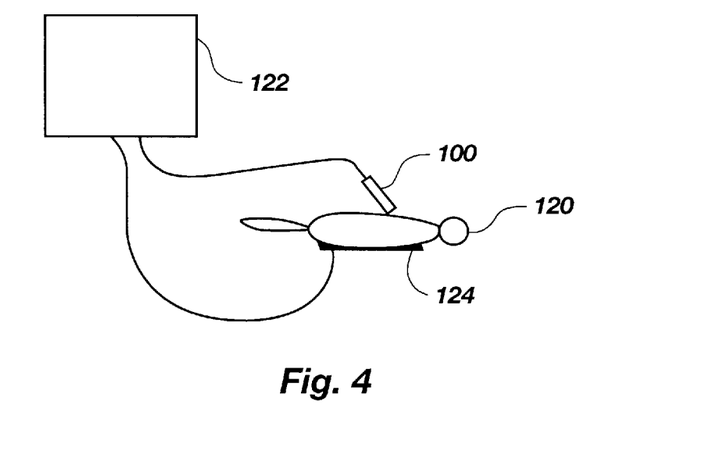
FIG. 4 is a block diagram of the components of the present invention as used in a monopolar mode.

The functions described above are accomplished using the preferred embodiment of the electrosurgical blade 100 as shown in FIG. 2A, in conjunction with the apparatus as shown in FIG. 4. The block diagram shows that the electrosurgical blade 100 is used in the same manner as prior art electrosurgical blades. For example, in a monopolar mode, a patient 120 lies on a large return electrode 124 which soaks up the electrical current introduced by the electrosurgical blade 100. An electrosurgical unit (ESU) 122 supplies the radio frequency energy to the electrosurgical blade 100. Thus it is easy to identify the path of the electrical energy from the ESU 122 to the electrosurgical blade 100, from the electrosurgical blade 100 to the patient 120, from the patient 120 to the return electrode 124, and from the return electrode 124 back to the ESU 122.

Conventional electrosurgical blades operate such that it is necessary or desirable to use electrodes of different shapes in order to accomplish all of the electrosurgical functions described earlier. For example, common shapes are the loop, square, ball, blade, triangle, diamond and needle. The electrosurgical blade 100 of the present invention, however, is able to accomplish all of the electrosurgical functions. (all these shapes will be covered)

In comparison, the function of coagulation in the prior art is typically performed using a thin wire. Therefore the process is slow and tedious, and ultimately results in less effective coagulation. Furthermore, the thin wire is not suitable for other electrosurgical functions. By contrast, the electrosurgical blade 100 performs coagulation using the full flat face 116. The advantage is that a larger surface area of tissue can be coagulated simultaneously, thus providing faster and more effective coagulation, thus reducing the surgical time.

The function of fulguration to achieve hemostasis is a previously highlighted goal of the present invention. Once an effective incision is made using a cutting edge 114, but the co-process of hemostasis is inadequate, the clinician may encounter active hemorrhage at the site. The spark-gap distance (distance between the electrosurgical blade 100 and the tissue) must be sufficiently great to accommodate the clinician's depth perception. In other words, if the spark-gap distance is too small, the clinician may have difficulty fulgurating and may touch the tissue. At the voltage of fulguration, desiccation is then likely to occur with deep thermal injury to the tissue. Therefore, the greater the spark-gap distance for a given power setting, the easier the fulguration becomes for the clinician and the less likely inadvertent excessive thermal damage is to occur.

The fact that the present invention can perform fulguration is also a distinct advantage over the prior art because this function damages the coating on the electrosurgical blades of the prior art. This is because the spark has such a concentrated current density. The high current density serves to poke holes through other coatings, mainly because the other coatings are typically not electrically conductive themselves, such as Teflon™. Repeated fulguration will eventually ruin Teflon™ coated blades. In contrast, the TiN ceramic coating 104 is not degraded by fulguration because the spark is being conducted by the TiN instead of the TiN acting as an obstruction which a spark must penetrate by physically creating larger and larger holes.

In summary, the electrosurgical blade 100 of the present invention provides many unique advantages over the prior art. The TiN ceramic coating 104 on the electrosurgical blade 100 provides a blade which can perform all the functions of cutting, coagulation, fulguration and desiccation, where the fulguration process does not destroy the TiN ceramic coating 104. The TiN ceramic coating 104 is able to easily glide through tissue, minimizing the build up of charred tissue to thereby provide a more uniform and consistent cut. The TiN ceramic coating 104 does not significantly wear or burn off, thereby providing improved reliability and durability, and not evolving by-product gases. The TiN ceramic coating 104 increases patient, clinician and staff safety by reducing the amount of current which must be used because the electrosurgical blade 100 more effectively reduces tissue build up. The TiN ceramic coating 104 also does not require any more current than conventional stainless steel blades. By keeping current low, damage to surrounding tissue by heat (thermal spread) is minimized.

Advantageously, the TiN ceramic coating 104 can also be repeatedly cleaned enabling the electrosurgical blade 100 to be reused many times. Furthermore, many different sterilization techniques can be used without damaging the TiN coating.

The electrosurgical blade 100 itself can also be used to cauterize tissue on its full flat face 116. Because it is an amorphous coating, the electrosurgical blade 100 can also be bent to perform more surgical procedures without damaging it. By reducing tissue build up, plumes are reduced, as well as foreign body contamination of the surgical field. Finally, the electrosurgical blade 100 is a low-cost design which can be manufactured using a relatively simple process.

While the presently preferred embodiment teaches that the preferred substrate is stainless steel, it should be apparent that other materials can also be used. These other materials might also be conductive metals such as titanium, but can also include non-conductive materials such as plastics. While the use of plastic probably eliminates the possibility of having an amorphous coating between the ceramic and the substrate, it can still provide some of the advantages of the presently preferred embodiment.

A final advantage to consider concerns the manufacturing process for the electrosurgical blade 100. In a preferred embodiment, the TiN ceramic coating 104 is applied to the stainless steel blade 106 using a room temperature direct sputtering process. Sputtering is a room or relatively low temperature process by which a controlled thin film of Titanium Nitride is uniformly deposited on the stainless steel blade 100.

The sputtering process itself is relatively simple, and has numerous advantages for the present invention. For example, the sputtering process does not change the characteristics of the base metal substrate 102 or the TiN ceramic coating 104. The other advantages become obvious with an examination of the sputtering process.

There are two forms of sputtering which are described herein to create the electrosurgical blade 100 of the present invention. The first form of sputtering is known as direct sputtering. This means that the sputtering is done directly from a TiN source. TiN sources are available commercially, and pure TiN can be coated onto the base metal substrate 102 using radio frequency sources in a non-reactive atmosphere.

Another method of applying TiN to the base metal substrate 102 is through the process of reactive sputtering. In this process, the reactive atmosphere must be composed of nitrogen. The titanium reacts with the nitrogen atmosphere to form titanium nitride. The TiN then coats the surface of the stainless steel blade 106.

Figure 5:
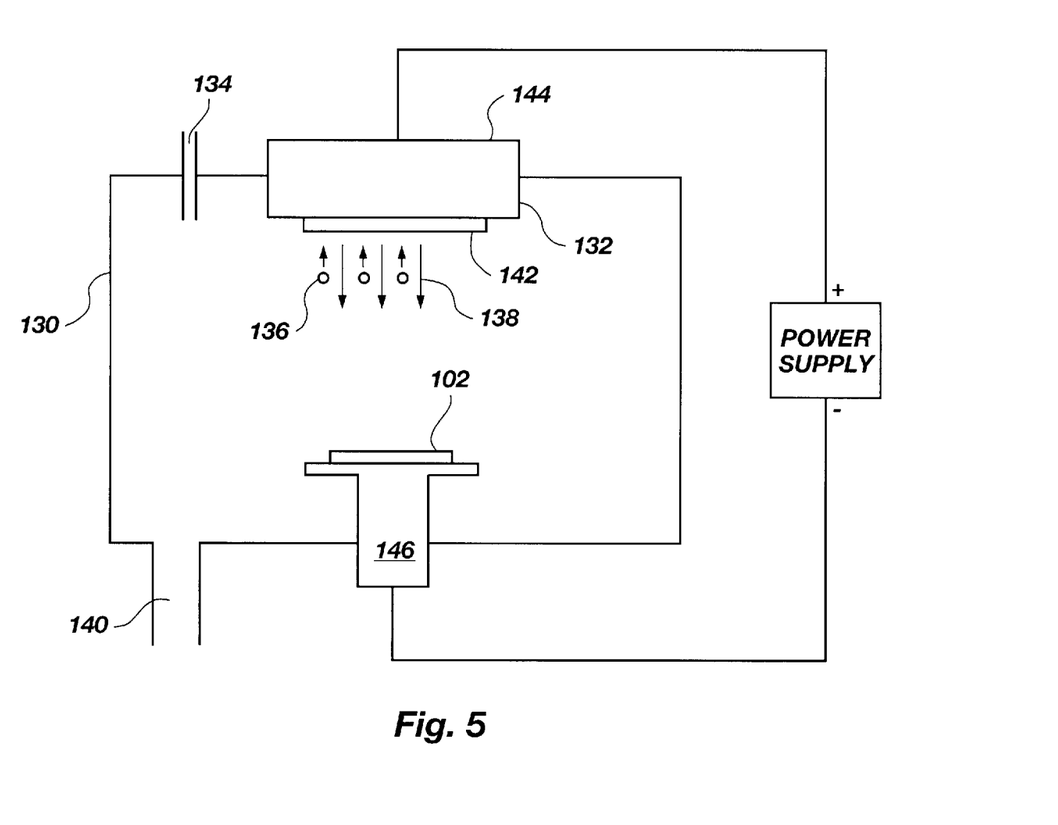
FIG. 5 is a schematic diagram of a sputtering chamber used in the direct sputtering manufacturing process of the present invention.

The process of both direct and reactive sputtering involves much of the same equipment as shown in FIG. 5. The sputtering takes place in a stainless steel chamber 130. In this preferred embodiment, the stainless steel chamber 130 has dimensions of approximately 18 inches in diameter and 12 inches in height. The actual sputtering function is accomplished by sputtering guns 132 which are generally located at the top of the stainless steel chamber 130. The sputtering guns 132 are capable of movement in both the horizontal and vertical directions as desired.

The sputtering system described above is accomplished using standard equipment readily available for manufacturing. In a preferred embodiment, the sputtering equipment is used to manufacture an electrosurgical blade by direct sputtering. An example of the direct sputtering process is as follows. The stainless steel chamber 130 is evacuated of ambient air through evacuation port 140. An inert gas such as argon is then fed into the stainless steel chamber 130 through a gas port 134. The argon gas is ionized using the cathode 144 and the anode 146 to generate an ion flux 136 which strikes the Titanium Nitride 142. The impact of the ion flux 136 will eject TiN sputtered flux 138 which travels and adheres to the base metal substrate 102. It is important to note that there are other sputtering processes well known to those skilled in the art which are also appropriate for applying the TiN ceramic coating 104.

While sputtering times may vary, experimentally it has been determined that the sputtering time is generally 1 to 1.5 hours to generate a TiN ceramic coating 104 on the base metal substrate 102 which is approximately 0.5 microns thick. Generally it has been found that the sputtering process applies the TiN ceramic coating 104 according to a linear function, so the application time is easily adjusted accordingly to obtain the desired thickness. The 0.5 micrometer thick TiN coating thus corresponds to a TiN deposition rate of approximately 1 angstrom thickness being added every second. The presently preferred thickness of the TiN ceramic coating 104 is a range which varies between approximately 0.1 microns and 0.5 microns. The upper thickness range is only provided to emphasize that generally nothing more is gained by making the TiN ceramic coating 104 any thicker.

While the presently preferred method of application of the ceramic to the substrate is through sputtering, it should be apparent that there are other methods. These include such methods as CVD and plasma deposition. Therefore, the application method of sputtering should not be considered limiting in the present invention.

It should be mentioned that TiN also differs from other state of the art coatings for electrosurgical blades in that it does not evolve dangerous gases. When heated, TiN does not evolve any gases and thereby the patient and the surgical team are spared the additional hazards.

It is important to realize that in alternative embodiments of the present invention, a cutting edge does not have to be provided on the electrosurgical instrument. Specifically, when minimally invasive electrosurgical procedures are to be performed, the cutting/coagulation means can be accomplished using shapes including a loop, square, ball, blade, triangle, diamond and needle. While the electrosurgical blade 100 of the present invention is able to accomplish all of the electrosurgical functions previously described, it may be desirable not to include a cutting edge where it could otherwise cause unintended damage to tissue.

A specific example of a non-cutting edge is when an electrosurgical instrument is used in the bi-polar mode. As explained previously, the bipolar mode delivers electrical current to tissue which is disposed between at least two electrodes which are generally spaced apart to form a gap. Therefore, the shape of the at least two electrodes can be some type of forceps, tweezers or scissors.

It should also be mentioned that minimally invasive surgical procedures also include those which also require a cutting edge in the mono-polar mode. These minimally invasive procedures include such procedures as laparoscopy, endoscopy and cardioscopy.

While the presently preferred embodiment of the invention emphasize the amorphous coating of a ceramic on the electrosurgical blade, it should also be realized that crystalline coatings can also be used. While these electrosurgical surgical instruments might not be able to be used in surgical procedures requiring bending, they can still take advantage of such properties as the conductive nature of the coating.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. An electrosurgical instrument for use in surgical procedures where it is desired to cut or cauterize tissue utilizing radio frequency energy, and wherein the electrosurgical instrument is comprised of:

a substrate having at least one cutting edge, and wherein the substrate is adapted to be electrically coupled to a source of radio frequency energy which can be directed to the at least one cutting edge; and a continuous, conductive, ceramic coating disposed on the substrate to thereby cover the at least one cutting edge with an amorphous coating which can flex with the substrate without damaging the continuity of the continuous ceramic coating.

2. The electrosurgical instrument as defined in claim 1 wherein the substrate is further comprised of at least one cauterizing surface, wherein the continuous, conductive, ceramic coating is disposed on the at least one cauterizing surface, and wherein the radio frequency energy can be directed to the at least one cauterizing surface to thereby enable the at least one cauterizing surface to promote hemostasis of tissue with which it comes in contact.

3. The electrosurgical instrument as defined in claim 1 wherein the continuous ceramic coating is sufficiently conductive to enable fulguration of tissue by propagating a spark from the continuous ceramic coating to the tissue.

4. The electrosurgical instrument as defined in claim 1 wherein the continuous ceramic coating is selected from the group of ceramics consisting of transition metal nitrides of which some are (i) amorphous and (ii) conductive.

5. The electrosurgical instrument as defined in claim 1 wherein the continuous ceramic coating is comprised of at least two ceramics which are transition metal nitrides.

6. The electrosurgical instrument as defined in claim 1 wherein the continuous ceramic coating is comprised of (I) at least one ceramic which is a transition metal nitride, and (ii) at least one material which is not a transition metal nitride.

7. The electrosurgical instrument as defined in claim 1 wherein the substrate is composed of a conductive base metal.

8. The electrosurgical instrument as defined in claim 7 wherein the conductive base metal is stainless steel.

9. The electrosurgical instrument as defined in claim 1 wherein the continuous ceramic coating is deposited on the substrate to a thickness of at least 0.1 micrometers.

10. The electrosurgical instrument as defined in claim 1 wherein the continuous ceramic coating does not burn away after repeatedly performing the functions of cutting, cauterizing, fulguration and desiccation.

11. The electrosurgical instrument as defined in claim 1 wherein the at least one cutting edge has generally uniform electrical current density therealong when radio frequency energy is applied to thereto.

12. The electrosurgical instrument as defined in claim 2 wherein the at least one cauterizing surface has generally uniform electrical current density therealong when radio frequency energy is applied to thereto.

13. An electrosurgical instrument for use in surgical procedures where it is desired to coagulate utilizing radio frequency energy, and wherein the electrosurgical instrument is comprised of:

a substrate having a plurality of electrodes at a coagulating end thereof, and wherein the substrate is adapted to be electrically coupled to a source of radio frequency energy which can be directed to the electrodes so as to provide a first path for the radio frequency energy to travel to the electrodes, and a second path for the radio frequency energy to return from the electrodes; and a continuous, conductive, ceramic coating disposed on the substrate to thereby cover the electrodes with an amorphous coating which can flex with the electrodes without damaging the continuity of the continuous ceramic coating.

14. The electrosurgical instrument as defined in claim 13 wherein the plurality of electrodes have a shape of forceps, tweezers or scissors.

15. A method for providing an electrosurgical instrument that enables electrosurgical procedures to be performed while minimizing thermal damage to tissue, the method comprising the steps of:

a) disposing an amorphous, conductive, ceramic coating on an electrosurgical instrument, wherein the amorphous, conductive, ceramic coating resists build up of charred tissue thereon so that the at least one electrosurgical procedure can be performed using a minimum level of radio frequency energy applied to the electrosurgical instrument; and b) performing the functions of cutting, cauterizing, fulguration or desiccation during the electrosurgical procedures by using the electrosurgical instrument which minimizes thermal damage to tissue.

16. The method for performing the at least one electrosurgical procedure as defined in claim 15 wherein the step of disposing an amorphous ceramic coating includes the step of applying a ceramic coating from the group of ceramics consisting of transition metal nitrides of which some are (i) amorphous and (ii) conductive.

17. The method for performing at least one electrosurgical procedure as defined in claim 16 wherein the step of disposing an amorphous and ceramic coating includes the step of applying at least two ceramics which are transition metal nitrides.

18. The method for performing the at least one electrosurgical procedure as defined in claim 16 wherein the step of disposing an amorphous and ceramic coating includes the steps of applying:

(i) at least one ceramic which is a transition metal nitride; and (ii) at least one material which is not a transition metal nitride.

19. The method for performing the at least one electrosurgical procedure as defined in claim 15 wherein the method further includes the step of applying an amorphous ceramic coating which is not worn away by application of RE energy, by scrubbing or by repeated sterilization of the amorphous ceramic coating.

20. The method for performing the at least one electrosurgical procedure as defined in claim 15 wherein the method of performing at least one electrosurgical procedure includes the step of performing an electrosurgical procedure which requires that the electrosurgical instrument be deformed from a resting state, and wherein the amorphous ceramic coating is deformed with the electrosurgical instrument without damage to the amorphous ceramic coating.

21. The method for performing the at least one electrosurgical procedure as defined in claim 15 wherein the method further includes the step of minimizing plumes during the at least one electrosurgical procedure by preventing build up of charred tissue on the electrosurgical instrument by using an amorphous ceramic coating thereon.

22. The method for performing the at least one electrosurgical procedure as defined in claim 15 wherein the method further includes the step of reducing introduction of foreign body contamination in a surgical field by reducing build up of charred tissue on the electrosurgical instrument which can break away therefrom during the at least one electrosurgical procedure.

23. The method for performing the at least one electrosurgical procedure as defined in claim 15 wherein the method further includes the step of creating a controlled incision in the tissue by reducing build up of charred tissue on the electrosurgical instrument.

24. A method of manufacturing an electrosurgical instrument for use in surgical procedures where it is desired to cut or cauterize tissue utilizing radio frequency energy, the method comprising the steps of:

(1) providing a substrate having at least one cutting edge, and wherein the substrate is adapted to be electrically coupled to a source of radio frequency energy which can be directed to the at least one cutting edge; and (2) depositing a thin, conductive, continuous, amorphous ceramic coating on the substrate, wherein the thin, conductive, continuous, amorphous ceramic coating is capable of being deformed integrally with the electrosurgical instrument without sustaining damage thereto.

25. The method of manufacturing as defined in claim 24 wherein the method comprises the further step of depositing the amorphous ceramic coating using room or near room temperature sputtering.

26. The method of manufacturing as defined in claim 24 wherein the step of depositing the thin, conductive, continuous, amorphous coating further comprises the steps of:

(1) substituting titanium nitride as the coating; and (2) sputtering the titanium nitride onto the substrate.

27. An electrosurgical instrument for use in surgical procedures where it is desired to cut or cauterize tissue utilizing radio frequency energy, and wherein the electrosurgical instrument is comprised of:

a substrate having at least one means for cutting/coagulation, and wherein the substrate is adapted to be electrically coupled to a source of radio frequency energy which can be directed to the at least one cutting/coagulation means; and a continuous, conductive, ceramic coating disposed on the substrate to thereby cover the at least one cutting/coagulation means with an amorphous coating which can flex with the substrate without damaging the continuity of the continuous ceramic coating.

28. The electrosurgical instrument as defined in claim 27 wherein the at least one cutting/coagulation means is selected from the group of cutting/coagulation means consisting of a loop, square, ball, blade, triangle, diamond and needle.

29. An electrosurgical instrument for use in surgical procedures where it is desired to cut or cauterize tissue utilizing radio frequency energy, and wherein the electrosurgical instrument is comprised of:

a substrate having a working end, wherein the working end is adapted to be electrically coupled to a source of radio frequency energy which can be directed to the working end; and a continuous, conductive, ceramic coating disposed on the substrate to thereby cover the working end with an amorphous coating which can flex with the substrate without damaging the continuity of the continuous ceramic coating.

* * * * *

UNITED STATES PATENT AND TRADEMARK OFFICE
CERTIFICATE OF CORRECTION

PATENT NO : 5,925,043
DATED : July 20, 1999
INVENTOR(S) : B. Ajit Kumar, Don B. Olsen It is certified that error appears in the above-identified patent and that said Letters Patent is hereby corrected as shown below:

*Attorney, Agent, or Firm-* should read - - Morriss, Bateman, O'Bryant & Compagni, P.C. - -

The Figure published on the first page of the Letters Patent with the abstract should be the following:

Signed and Sealed this

Eleventh Day of January, 2000

Attest:

Q. TODD DICKINSON

Attesting Officer

Acting Commissioner of Patents and Trademarks

UNITED STATES PATENT AND TRADEMARK OFFICE
Certificate

Patent No. 5,925,043                                        Patented: July 20, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: B. Ajit Kumar, Salt Lake City, Utah; Don B. Olsen, Salt Lake City, Utah; Pratap Khanwilkar, New York, New York; and Sivaraman Guruswamy, Salt Lake City, Utah.

Signed and Sealed this Tenth Day of December 2002.

LINDA C. M. DVORAK
*Supervisory Patent Examiner*
Art Unit 3739